United States Patent [19]

Markwell et al.

[11] Patent Number: 5,891,887
[45] Date of Patent: Apr. 6, 1999

[54] USE OF [R-(Z)]-α-(METHOXYIMINO)-α-(1-AZABICYCLO [2.2.2.]OCT-3-YL) ACETONITRILE TO REDUCE AMYLOID βA4 FORMATION IN ALZHEIMER'S DISEASE

[76] Inventors: Roger Edward Markwell; Julie Hawkins; Carol Wendy Gray, all of SmithKline Beecham Corporation Corporate Intellectual Property—UW2220 P.O. Box 1539, King of Prussia, Pa. 19406-0939

[21] Appl. No.: 836,013
[22] PCT Filed: Oct. 17, 1995
[86] PCT No.: PCT/EP95/04082
  § 371 Date: Apr. 25, 1997
  § 102(e) Date: Apr. 25, 1997
[87] PCT Pub. No.: WO96/12486
  PCT Pub. Date: May 2, 1996

[30] Foreign Application Priority Data

Oct. 25, 1994 [GB] United Kingdom ............... 9421472

[51] Int. Cl.$^6$ ................................................. A61K 31/435
[52] U.S. Cl. ............................................................. 514/299
[58] Field of Search ............................................... 514/299

[56] References Cited

U.S. PATENT DOCUMENTS

| | | | |
|---|---|---|---|
| 5,242,932 | 9/1993 | Gandy et al. | 514/313 |
| 5,348,963 | 9/1994 | Gandy et al. | 514/313 |
| 5,385,915 | 1/1995 | Buxbaum et al. | 514/313 |

FOREIGN PATENT DOCUMENTS

| | | |
|---|---|---|
| 0 392 803 | 10/1990 | European Pat. Off. . |
| 0 457 295 A2 | 11/1991 | European Pat. Off. . |
| WO 93/11762 | 6/1993 | WIPO . |
| WO 94/09370 | 4/1994 | WIPO . |

OTHER PUBLICATIONS

Scott et al., "New Avenues for Therapeutic Intervention in Alzheimer's Disease", (1994), DN&P, vol. 7, No. 5, pp. 269–278.

Y. Lamour, "Alzheimer's disease: a review of recent findings", (1994), Biomed. and Pharmacother. vol. 48, pp. 312–318.

Buxbaum, et al., "Cholinergic agonists and interleukin 1 regulate processing and secretion of the Alzheimer β/A4 amyloid protein precursor", (1992), Proc. Natl. Acad. Sci. USA, vol. 89, pp. 10075–10078.

Buxbaum, et al., "Calcium regulates processing of the Alzheimer amyloid protein precursor in a protein kinase C–independent manner", (1994), Proc. Natl. Acad. Sci. USA, vol. 91, pp. 4489–4493.

Ensinger, et al., "WAL 2014—A Muscarinic Agonist With Preferential Neuron–Stimulating Properties", (1993), Life Sciences, vol. 52, Nos. 5&6, pp. 473–480.

Nitsch, et al., "Regulation of proteolytic processing of the amyloid β–protein precursor of Alzheimer's disease in the transfected cell lines and in brain slices", (1994), J. Neural Transm., vol. 44, pp. 21–27.

Nitsch, et al., "Role of Neurotransmission in the Regulation of Amyloid β–Protein Precursor Processing", (1994), Biochemical Pharmacology, vol. 47, No. 8, pp. 1275–1284.

Davis, et al., "Cholinergic Therapies for Alzheimer's Disease", (1995), Arzneim–Forsch/Drug Res., 45(1), pp. 425–431.

DeLapp et al., "The M1 Agonist Xanomeline Potently Stimulates Apps Release From CHO–m1 Cells" (1995), Abstracts, 6th Intl. Symposium on Subtypes of Muscarinic Receptors, Florida, USA (Nov. 1994), vol. 56, Nos. 11 & 12, p. 1024.

Davis, et al., "Muscarinic Control of Amyloid Precursor Protein (App) Processing: Involvement of Protein Kinase C (PKC) and Intracellular Ca", p. 110.

Davis, et al., "Therapeutic Intervention in Dementia", (1993), Critical Reviews in Neurobiology, vol. 71(1), pp. 41–83.

American Psychiatric Association, "Dementia", Diagnostic and Statistical Manual of Mental Disorders, pp. 132–155.

J.H. Growdon, "Muscarinic Agonists: Effect on APP Processing", (1994), Meeting Notes by MSG Clark, Given at Roundtable 6, 4th International Conference on Alzheimer's Disease and Related Disorders, Minneapolis.

Nitsch, et al., "Release of Alzheimer Amyloid Precursor Derivatives Stimulated by Activation of Muscarin Acetylcholine Receptors", (1992), Science, vol. 258, No. 5080, pp. 304–307.

Haring, et al., "Amyloid Precursor Protein Secretion Via Muscarinic Receptors: Reduced Desensitization Using the M1–Selective Agonist AF102B", (1994), Biochemical and Biophysical Research Communications, vol. 203, No. 1, pp. 652–658.

Felder, et al., "Muscarinic Acetylcholine Receptor Subtypes Associated with Release of Alzheimer Amyloid Precursor Derivatives Activate Multiple Signal Transduction Pathways", (1993), Annals New York Academy of Sciences, vol. 695, pp. 15–18.

Nitsch, et al., "Receptor–coupled Amyloid Precursor Protein Processing", (1993), Annals New York Academy of Sciences, vol. 695, pp. 122–127.

Hung, et al., "Activation of Protein Kinase C Inhibits Cellular Production of the Amyloid β–Protein", (1993), J. of Biological Chemistry, vol. 268, No. 31, pp. 22959–22962.

*Primary Examiner*—James H. Reamer
*Attorney, Agent, or Firm*—Linda E. Hall; Stephen A. Venetianer; Charles M. Kinzig

[57] ABSTRACT

A method of enhancing amyloid precursor protein processing along a non-amyloidogenic pathway in patients suffering from, or at risk of developing, Alzheimer's disease and a method of treatment or prophylaxis of Alzheimer's disease by reducing βA4 production in patients suffering from, or at risk of developing, Alzheimer's disease comprising administering to the patient an effective, non-toxic amount of an acetonitrile compound, use of the compound in preparation of a medicament for use in the method and a composition for use in the method.

4 Claims, No Drawings

USE OF [R-(Z)]-α-(METHOXYIMINO)-α-(1-AZABICYCLO [2.2.2.]OCT-3-YL) ACETONITRILE TO REDUCE AMYLOID βA4 FORMATION IN ALZHEIMER'S DISEASE

This invention relates to a method for enhancing amyloid precursor protein processing along a non-amyloidogenic pathway and to a compound for use in such method.

Amyloid precursor protein (APP) is an integral membrane glycoprotein that can be processed in several ways. Cleavage by β and γ secretases ultimately leads to release of β amyloid protein (βA4) which is deposited in the brains of individuals with Alzheimer's disease (AD). Alternative cleavage by α secretase leads to the release of non-amyloidogenic APP fragments. The muscarinic agonists carbachol, bethanechol, AF-102B and xanomeline have been shown to enhance the production of non-amyloidogenic APP fragments by activation of m1 and/or m3 receptor subtypes (Nitsch et al 1992, Buxbaum et al 1992, 1994, Haring et al 1994, Growdon 1994).

EP-A-0392803 (Beecham Group p.l.c.) discloses certain azabicyclic compounds which enhance acetylcholine function via an action at muscarinic receptors within the central nervous system, including [R-(Z)]-α-(methoxyimino)-α-(1-azabicyclo[2.2.2]oct-3-yl)acetonitrile (Compound (I)), and pharmaceutically acceptable salts, and processes by which such compounds may be made.

WO-93/17018 discloses alternative processes by which Compound (I) may be made.

It has now been discovered that Compound (I) enhances amyloid precursor protein processing along a non-amyloidogenic pathway and is therefore of potential use in the treatment of Alzheimer's disease by reducing βA4 production.

According to the present invention, there is provided the use of Compound (I) or a pharmaceutically acceptable salt thereof in the manufacture of a medicament for enhancing amyloid precursor protein processing along a non-amyloidogenic pathway in patients suffering from, or at risk of developing, Alzheimer's disease. The invention further provides the use of Compound (I) or a pharmaceutically acceptable salt thereof in the treatment or prophylaxis of Alzheimer's disease by reducing βA4 production.

In a further aspect the invention provides a method of enhancing amyloid precursor protein processing along a non-amyloidogenic pathway in patients suffering from, or at risk of developing, Alzheimer's disease comprising administering to the patient an effective, non-toxic amount of Compound (I) or a pharmaceutically acceptable salt thereof. The invention further provides a method of treatment or prophylaxis of Alzheimer's disease by reducing βA4 production in patients suffering from, or at risk of developing, Alzheimer's disease comprising administering to the patient an effective, non-toxic amount of Compound (I) or a pharmaceutically acceptable salt thereof.

Compound (I) can form acid addition salts with strong acids. The term pharmaceutically acceptable salt encompasses solvates and hydrates.

Compound (I) is preferably provided in a pharmaceutical composition, which comprises Compound (I) or a pharmaceutically acceptable salt thereof, and a pharmaceutically acceptable carrier.

The composition may be in the form of tablets, capsules, powders, granules, lozenges, suppositories, reconstitutable powders, or liquid preparations such as oral or sterile parenteral solutions or suspensions.

In order to obtain consistency of administration it is preferred that a composition is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

Solid oral compositions may be prepared by conventional methods of blending, filling, tabletting or the like. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, or hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The composition may contain from 0.1% to 99% by weight, preferably from 10–60% by weight, of the active material, depending on the method of administration.

The invention additionally provides a pharmaceutical composition as above defined for use in enhancing amyloid precursor protein processing along a non-amyloidogenic pathway in patients suffering from, or at risk of developing, Alzheimer's disease. The invention further provides a pharmaceutical composition as above defined for use in the treatment and/or prophylaxis of Alzheimer's disease by reducing βA4 production.

The dose of the compound will vary in the usual way with the seriousness of the disorder, the weight of the sufferer, and the relative efficacy of the compound.

However, as a general guide suitable unit doses may be 5 to 300 μg, for example 10 to 200 μg and such unit doses may be administered more than once a day, for example two or three times a day, so that the total daily dosage is in the range of about 30 to 600 μg and such therapy may well extend for a number of years.

Within the above indicated dosage ranges no unacceptable toxicological effects are indicated for Compound (I).

The following pharmacological data illustrates the invention.

PHARMACOLOGICAL DATA

Amyloid precursor protein processing CHO cells

The effect of test compound on APP processing in Chinese hamster ovary (CHO) cells, transfected with human muscarinic receptors, was investigated using Western blotting techniques. Blots were quantified using a laser densitometer to scan the immunoreactive bands.

Materials

The CHO cells stably transfected with human muscarinic receptors (Bonner 1988) were obtained from N.I.M.H. (Md. USA). Tissue culture media and reagents were from Gibco BRL (Scotland). General laboratory reagents were from Sigma Chemical Co. (Dorset). [R-(Z)]-α-(methoxyimino)-α-(1-azabicyclo [2.2.2]oct-3-yl)acetonitrile monohydrochloride is described in EP-A-0392803 as the oxalate salt.

The following primary antibodies were used: 22C11 mouse monoclonal antibody (Boehringer Mannheim, Sussex, UK) which recognises an amino terminal epitope of APP (Weidemann et al, 1989); anti βA4 1–25 rabbit polyclonal antibody raised against rat βA4 1–25; Ab54 rabbit polyclonal antibody raised against a carboxy terminal epitope of APP (amino acids 751–770 of APP770).

The secondary antibodies were anti rabbit or anti mouse IgG (Sigma Chem. Co., Dorset, UK) followed by rabbit or mouse peroxidase anti peroxidase (PAP) (Sigma Chem. Co., Dorset, UK). The substrate used was the enhanced chemiluminescence kit (ECL) (RPN2106, Amersham, Bucks, UK) and immunoreactive bands were detected using Hyperfilm-ECL (Amersham, Bucks, UK).

Methods

Cell culture

CHO cells transfected with human muscarinic receptor subtypes hm1, hm2, hm3 and hm4 were grown to confluence on tissue culture dishes (10 cm diameter) in α-Minimum Essential Medium (αMEM) with ribonucleosides and deoxyribonucleosides, 10% foetal calf serum, penicillin 100 units/ml and streptomycin 100 μg/ml.

Cell treatment with test compound

Cells were grown to confluence as above then serum containing medium was removed followed by washing the cells twice in 5 ml serum free medium. The cells were then treated with 5 ml serum free medium containing the appropriate concentration of test compound and incubated at 37° C. for three hours.

The conditioned media was collected, placed on ice and protease inhibitors added (1 mM phenylmethylsulfonyl fluoride (PMSF), 5 mM ethylenediaminetetraacetic acid (EDTA),1 ug/ml leupeptin). The media was then centrifuged for 15 minutes at 3000 G and 4° C. to remove cell debris. The supernatant was removed and concentrated 100 fold using Centricon 10 concentrators (Amicon, Gloucestershire, UK) by centrifuging at 3000 G for 90 minutes at 4° C. The retentate was collected and stored in aliquots at −20° C. until ready for electrophoresis. The cells were washed twice with 5 ml serum free medium, scraped and centrifuged for 5 minutes at 3000 G and 4° C. to obtain a cell pellet. The supernatant was removed and the cell pellet resuspended in 6×volume lysis buffer (0.1M Tris pH7.5 containing 1% Triton X100, 5 mM EDTA, 1 mM PMSF, 1 ug/ml leupeptin). The lysate was kept on ice for 30 minutes with intermittent vortexing followed by centrifuging for 5 minutes at 10000 G and 4° C. to remove cell debris. The supernatant was collected and stored in aliquots at −20° C. until ready for electrophoresis.

Protein Assay

Cell lysate and concentrated culture media samples were assayed for protein before gel electrophoresis to ensure equal protein loading between treatments on the gel. The proteins were measured by the Bradford dye-binding procedure (Bradford, 1976) using Bio-Rad (Herts, UK) dye reagent concentrate. The assay was carried out in a microtitre plate with the absorbance read at 590 nm using a Titretek Multiskan Plus MkII plate reader with software to analyse the results. As various reagents, particularly detergents, interfere with the Bradford assay calibrations were carried out in the appropriate sample vehicle.

SDS-PAGE

Proteins were fractionated using a Novex mini-gel system (R & D Systems Europe Ltd, Oxon, UK). An equal amount of protein was loaded to compare between treatments on the same gel. Samples were diluted in 2×reducing sample buffer containing 0.1M Tris pH6.8, 10% sodium dodecyl sulphate (SDS), 0.1% bromophenol blue in glycerol and 50% β-mercaptoethanol. The proteins were separated on a 6% Tris-glycine polyacrylamide gel containing SDS (Laemmli, 1970) for 90 minutes at 100 volts. Protein standards were also included of known molecular weight (Sigma).

Western Blot Analysis

After SDS-PAGE the gels were washed for 20 minutes in transfer buffer containing 2.5 mM Tris, 19.2 mM glycine, 20% methanol at pH 8.3. The proteins were transferred from the gel onto Immobilon P Polyvinylidine difluoride (PVDF) membrane (Millipore, Herts, UK) using a Bio-rad semi-dry system for 2 hours at 0.8 mA/cm$^2$. After transfer the proteins were visualised on the membrane by staining with a 10% solution of Ponceau S (Sigma) for 2 minutes. This was destained by rinsing with distilled water.

The membrane was blocked in phosphate buffered saline (PBS) containing 0.1% Tween 20 and 5% dried milk powder for at least 1 hour at room temperature. This was followed by two 30 second washes in PBS 0.1% Tween 20 (PBST) and then primary antibody was incubated overnight at 4° C. All antibodies were prepared in PBST containing 2% bovine serum albumin (Sigma). Membranes were washed in PBST for 1 minute followed by two 5 minute washes. Secondary antibody, anti-mouse or anti-rabbit IgG (Sigma), was added at 1/3000 or 1/5000 dilution respectively for 1 hour at room temperature. Membranes were washed as above and mouse or rabbit peroxidase anti peroxidase (Sigma) added at 1/3000 dilution for 1 hour at room temperature. A final wash step was in PBS only and then membranes were transferred to a clean dish to add ECL substrate (Amersham). The immunoreactive bands were detected on Hyperfilm-ECL (Amersham) which was developed using an automated processor (Kodak).

Densitometric Analysis

Changes in levels of APP were measured using a laser densitometer. Immunoreactive APP bands were scanned using a Pharmacia LKB Ultrascan XL linked to a computer with Gelscan XL software for processing data. The laser beam passed through the sample and the amount of light transmitted was measured by the photodiode thereby determining how much was absorbed. The absorbance readings were integrated to give values of area under the curve. Results for vehicle and test compound are expressed as the mean of 3 experiments±the standard error of the mean (SEM).

Ligand Binding Studies in vitro

Cerebral cortex was dissected from male Hooded Lister rats (Olac, U.K.) into 2.5 volumes (compared with wet weight) ice cold 50 mM tris pH 7.7. This was homogenised then centrifuged at 24,000 g for 15 minutes at 4° C. The pellet was resuspended in 2.5 vols and the homogenates were stored in 1 ml aliquots at −20° C. until required.

Incubations for [$^3$H]-OXO-M binding were prepared in a total volume of 2 ml of ice cold 50 mM Tris, containing 2 mM magnesium chloride. [$^3$H]-OXO-M acetate (New England Nuclear, specific activity 87 Ci/mmol) was added to a concentration of 1.88 nM. Cortex homogenate was at a final concentration of 300 vols based on the original wet weight (equivalent to 0.145 mg protein/ml). Non-specific binding was defined using 10 micromolar (uM) oxotremorine sesquifumarate. Incubations were carried out to equilibrium at 37° C. for between 30 and 45 mins. Samples were filtered through Watman GF/B filters pre-soaked for 30 minutes in a 0.05% aqueous solution of polyethylenimine to prevent adsorption of [$^3$H]-OXO-M to the glass fibre.

[$^3$H]-QNB, specific activity 44 Ci/mmol, final conc. 0.27 nM) binding was carried out similarly except that the magnesium chloride was omitted and the dilution of the homogenate was increased to 1500 vols (7.8 ug protein/ml). Non-specific binding was defined with 1 uM atropine sulphate.

Binding data for the compound under study are provided in Table 5.

Results

Using the above methods, the effects of the test compound, Compound (I) monohydrochloride, was investigated on amyloid precursor protein processing.

Full length APP with a molecular weight of 108 kD and two bands of secreted APP with molecular weights of 108 kD and 118 kD were detected in all the transfected CHO cells.

CHOhm1

Full length APP in the cell membrane was decreased by Compound (I) monohydrochloride over the dose range $10^{-6}$–$10^{-4}$M after 3 hours treatment. In culture medium, test compound increased secreted APP 6–10 fold over the concentration range (Table 1).

CHOhm2

There was no change in full length APP in the cell membrane but secreted APP doubled in culture medium following treatment with $1\times10^{-4}$M Compound (I) monohydrochloride for 3 hours (Table 2).

CHOhm3

Full length APP in the cell membrane was decreased by Compound (I) monohydrochloride over the dose range $10^{-6-10-4}$M after 3 hours treatment. In culture medium, test compound increased secreted APP, approximately 20-fold over the concentration range (Table 3).

CHOhm4

There was no change in full length APP in the cell membrane or in secreted APP in culture medium following treatment with $1\times10^{-4}$M Compound (I) monohydrochloride for 3 hours (Table 4).

Ligand Binding Studies

Ligand binding data (Table 5) show that Compound (I) monohydrochloride possesses a QNB/OXO-M ratio of 22, indicative of partial agonist properties (Brown et al. 1988).

Conclusion

Compound (I) monohydrochloride alters APP processing by stimulation of m1 and m3 receptor subtypes. The enhanced release of secreted APP, particularly as detected with anti βA4 1–25 antibody (which should not recognise β secretase cleaved APP), strongly suggests this to be along a non-amyloidogenic pathway.

Thus Compound (I) monohydrochloride has potential utility in the treatment of Alzheimer's disease by reducing βA4 production in the brain as a result of increased non-amyloidogenic APP processing.

REFERENCES

Bonner T (1988) NIH Patent No. PB89-125652; U.S. application Ser. No. 7-241 971 filed Aug. 09, 1988
Bradford, M. (1976) Anal. Biochem., 72, 248–254
Brown, F., Clark, M., Graves, D., Hatcher, J., McArthur, R., Riley, G. and Semple, J. (1988) Drug Dev Res, 14, 343–347
Buxbaum, J. D., Oishi, M., Chen, H. I., Pinkas-Kramarski, R., Jaffe, E. A., Gandy, S. E. and Greengard, P. (1992) Proc. Natl. Acad. Sci., 89, 10075–10078
Buxbaum, J. D., Ruefli, A. A., Parker, C. A., Cypress, A. M. and Greengard, P. (1994) Proc. Natl. Acad. Sci., 91, 4489–4493
Growdon J. H. (1994) "Muscarinic agonists: Effects on APP processing" 4th International Meeting on Alzheimer's Disease, Minneapolis, July 1994.
Haring, R., Gurwitz, D., Barg, J., Pinkas-Kramarski, R., Heldman, E., Pittel, Z., Wengier, A., Meshulam, H., Marciano, D., Karton, Y. and Fisher, A. (1994) Biochem. Biophys. Res. Comm. 203(1), 652–658
Laemmli, U. K. (1970) Nature, 227, 680–685
Nitsch, R. M., Slack, B. E., Wurtman, R. J. and Growdon, J. H. (1992) Science, 258, 304–307
Weidemann, A., Konig, G., Bunke, D., Fischer, P., Salbaum, J. M., Masters, C. L. and Beyreuther, K. (1989) Cell, 57, 115–126

In the Tables

Table 1
CHOhm1 Dose Response
Results are the mean of three experiments and expressed as changes from control APP levels. (A 1-fold increase in secreted APP=no change from basal). Antibodies used were Ab54 in the cell lysates to detect full length APP and 22C11 to detect secreted APP.

Table 2
CHOhm2 Response
The antibodies used were as in Table 1. Results are the mean of three experiments and expressed as changes from control APP levels. (A 1-fold increase in secreted APP=no change from basal).

Table 3
CHOhm3 Dose Response
Antibodies used were Ab54 in the cell lysates to detect full length APP and anti βA4 1–25 to detect secreted APP. The experiments were carried out in triplicate. The results are the mean of three experiments and expressed as changes from control APP levels. (A 1-fold increase in secreted APP no change from basal).

Table 4
CHOhm4 Response
The antibodies used were as in Table 3. Results are the mean of three experiments and expressed as changes from control APP levels. (A 1-fold increase in secreted APP=no change from basal).

TABLE 5

Ligand Binding Data for Compound (I)

| | [$^3$H]-OXO-M IC50 | [$^3$H]-QNB IC50 | QNB/OXO-M |
|---|---|---|---|
| Compound (I)* | 14 | 309 | 22 |

*monohydrochloride

OXO-M=Oxotremorine-M, agonist ligand

QNB=Quinuclidinylbenzilate, antagonist ligand

QNB/OXO-M ratio is a guide to the functional efficacy of the compounds. Ratios greater than 100 are associated with full agonists, antagonists give ratios close to unity and intermediate values indicate partial agonists.

TABLE 1

CHOhm1 Dose Response

| | Blot Density (AUC mm$^2$) (±SEM) | Mean % Decrease in Full Length APP | Blot Density (AUC mm$^2$) (±SEM) | Mean Fold Increase in Secreted APP |
|---|---|---|---|---|
| Control | 23.74 ± 6.84 | | 2.29 ± 1.21 | |
| Compound (I)* 1 × 10 − 4M | 14.03 ± 7.27 | 40.9 | 17.54 ± 9.78 | 7.7 |
| 1 × 10 − 5M | 12.32 ± 5.91 | 48.1 | 14.48 ± 7.25 | 6.3 |
| 1 × 10 − 6M | 16.84 ± 7.20 | 29.1 | 24.2 ± 11.61 | 10.6 |

*monohydrochloride

TABLE 2

CHOhm2 Response

| | Blot Density (AUC mm$^2$) (± SEM) | Mean % Decrease in Full Length APP | Blot Density (AUC mm$^2$) (±SEM) | Mean Fold Increase in Secreted APP |
|---|---|---|---|---|
| Control | 12.61 ± 1.0 | | 2.74 ± 0.55 | |
| Compound (I)* 1 × 10$^{-4}$M | 12.04 ± 2.56 | 4.5 | 5.75 ± 1.60 | 2.1 |

*monohydrochloride

TABLE 3

CHOhm3 Dose Response

| | Blot Density (AUC mm$^2$) (± SEM) | Mean % Decrease in Full Length APP | Blot Density (AUC mm$^2$) (±SEM) | Mean Fold Increase in Secreted APP |
|---|---|---|---|---|
| Control | 23.06 ± 3.78 | | 0.85 ± 0.18 | |
| Compound (I)* 1 × 10 − 4M | 4.95 ± 1.14 | 78.5 | 15.81 ± 7.87 | 18.6 |
| 1 × 10 − 5M | 5.51 ± 1.18 | 76.1 | 15.60 ± 2.27 | 18.4 |
| 1 × 10 − 6M | 7.46 ± 3.36 | 67.7 | 16.33 ± 5.37 | 19.2 |

*monohydrochloride

TABLE 4

CHOhm4 Response

| | Blot Density (AUC mm$^2$) (± SEM) | Mean % Decrease in Full Length APP | Blot Density (AUC mm$^2$) (±SEM) | Mean Fold Increase in Secreted APP |
|---|---|---|---|---|
| Control | 25.24 ± 0.68 | | 20.80 ± 4.42 | |
| Compound (I)* 1 × 10$^{-4}$M | 24.62 ± 0.94 | 2.5 | 22.59 ± 10.28 | 1.1 |

*monohydrochloride

We claim:

1. A method of enhancing amyloid precursor protein processing along a non-amyloidogenic pathway in patients suffering from, or at risk of developing, Alzheimer's disease comprising administering to the patient an effective, non-toxic amount of [R-(Z)]-α-(methoxyimino)-α-(1-azabicyclo[2.2.2]oct-3-yl)acetonitrile or a pharmaceutically acceptable salt thereof.

2. A method of treatment or prophylaxis of Alzheimer's disease by reducing βA4 production in patients suffering from, or at risk of developing, Alzheimer's disease comprising administering to the patient an effective, non-toxic amount of [R-(Z)]-α-(methoxyimino)-α-(1-azabicyclo[2.2.2]oct-3-yl)acetonitrile or a pharmaceutically acceptable salt thereof.

3. A method according to claim 3 wherein the pharmaceutically acceptable salt is the monohydrochloride.

4. A method according to claim 2 wherein the pharmaceutically acceptable salt is the monohydrochloride.

* * * * *